United States Patent
Contolini et al.

(10) Patent No.: US 10,445,467 B2
(45) Date of Patent: Oct. 15, 2019

(54) SYSTEM AND METHOD TO RESTRICT THE OPERATIONAL RANGE OF WIRELESS DEVICES

(71) Applicant: KARL STORZ Imaging, Inc., Goleta, CA (US)

(72) Inventors: Matteo Contolini, Santa Barbara, CA (US); Ted Applebaum, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 638 days.

(21) Appl. No.: 15/071,135

(22) Filed: Mar. 15, 2016

(65) Prior Publication Data

US 2017/0270261 A1   Sep. 21, 2017

(51) Int. Cl.
| | | |
|---|---|---|
| *G06F 19/00* | (2018.01) |
| *H04W 4/021* | (2018.01) |
| *H04W 4/02* | (2018.01) |
| *G16H 40/63* | (2018.01) |
| *H04W 76/14* | (2018.01) |

(52) U.S. Cl.
CPC .......... *G06F 19/3418* (2013.01); *G06F 19/00* (2013.01); *G16H 40/63* (2018.01); *H04W 4/021* (2013.01); *H04W 4/023* (2013.01); *H04W 76/14* (2018.02)

(58) Field of Classification Search
None
See application file for complete search history.

(56) References Cited

U.S. PATENT DOCUMENTS

| | | | | |
|---|---|---|---|---|
| 6,563,430 B1* | 5/2003 | Kemink | ........... | H04B 1/202 340/12.22 |
| 7,463,813 B2* | 12/2008 | Zwart | ........... | A61B 6/00 235/375 |
| 7,768,420 B2* | 8/2010 | Neogi | ........... | G08C 23/04 340/10.2 |
| 7,846,150 B2* | 12/2010 | Hamel | ........... | A61B 17/32006 606/1 |
| 8,125,318 B2* | 2/2012 | Heimbrock | ........... | A61B 6/0457 340/12.22 |
| 8,175,590 B2* | 5/2012 | Hamel | ........... | A61B 1/00016 455/419 |
| 8,674,826 B2* | 3/2014 | Becker | ........... | A61B 5/0002 340/539.12 |
| 9,264,801 B2* | 2/2016 | Contolini | ........... | G06F 19/34 |
| 9,740,826 B2* | 8/2017 | Raghavan | ........... | G06F 19/3418 |
| 9,855,110 B2* | 1/2018 | Bitan | ........... | A61M 1/14 |

(Continued)

*Primary Examiner* — Michael Tomaszewski
(74) *Attorney, Agent, or Firm* — The Culbertson Group, P.C.; Nathan H. Calvert

(57) ABSTRACT

Methods and systems are provided for pairing a command device to a remotely controlled medical system. A command device is paired to a remotely controlled system, to control one or more medical devices from the command device. Registering the command device is done at a registration component at a designated location in an operating area, with an identifier for the operating area. While registered, the command device is able to transmit commands for controlling the medical equipment. The command device location is repeatedly estimated from its sensors based on markers or beacons in the operating area, to determine if it has left the area. Upon leaving, it is deregistered.

20 Claims, 11 Drawing Sheets

(56) References Cited

U.S. PATENT DOCUMENTS

| | | | | |
|---|---|---|---|---|
| 2003/0025604 A1* | 2/2003 | Freeman | ............. | A61B 5/7475 |
| | | | | 340/573.1 |
| 2003/0093503 A1* | 5/2003 | Yamaki | .................. | G06F 19/00 |
| | | | | 709/220 |
| 2009/0300507 A1* | 12/2009 | Raghavan | ........... | G06F 19/3418 |
| | | | | 715/738 |
| 2014/0153747 A1* | 6/2014 | Contolini | ................ | G06F 19/34 |
| | | | | 381/122 |
| 2015/0082542 A1* | 3/2015 | Hayes | ................... | A61G 7/018 |
| | | | | 5/600 |
| 2015/0364035 A1* | 12/2015 | Bruederle | ............. | G08C 17/02 |
| | | | | 340/12.22 |

\* cited by examiner

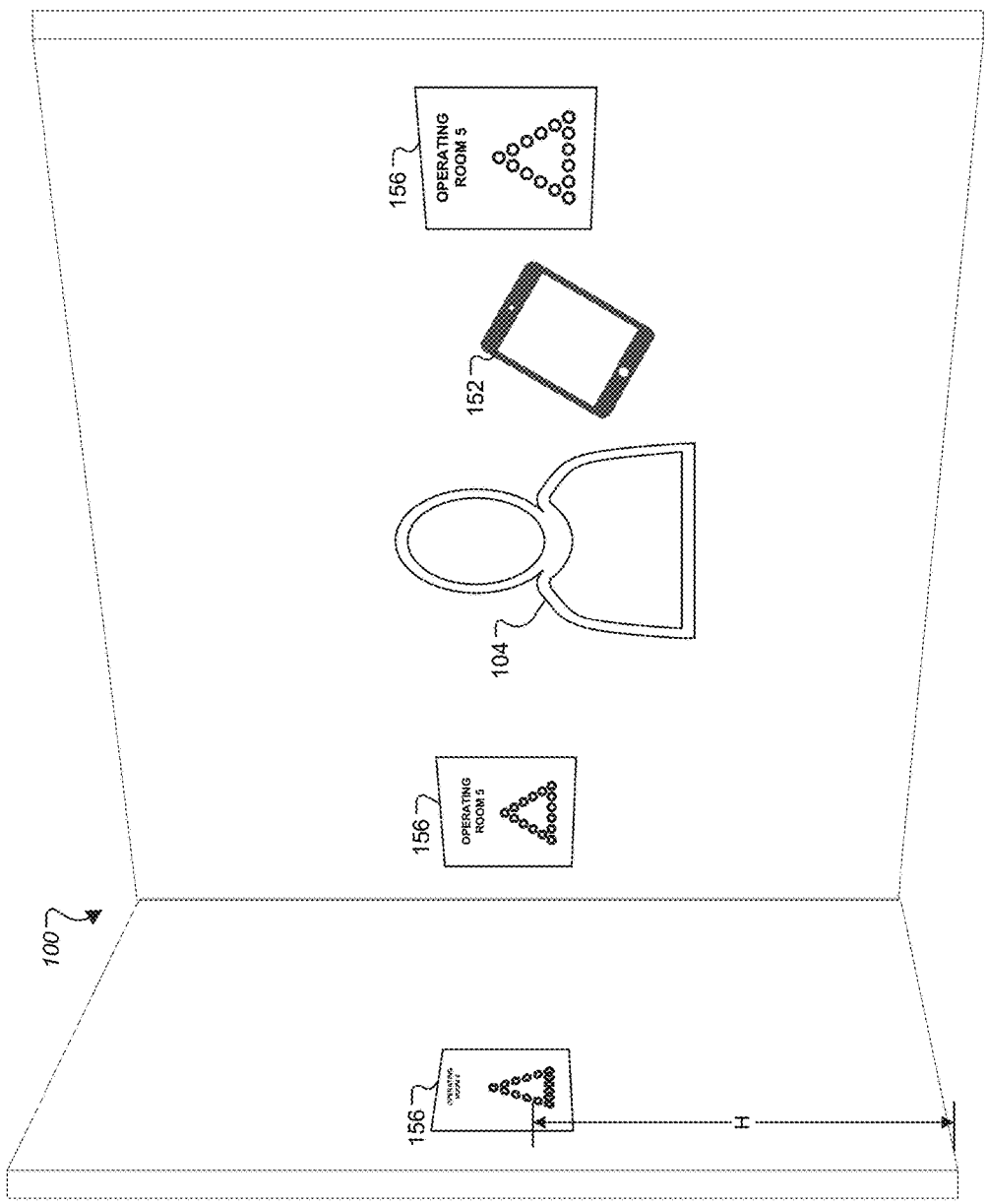

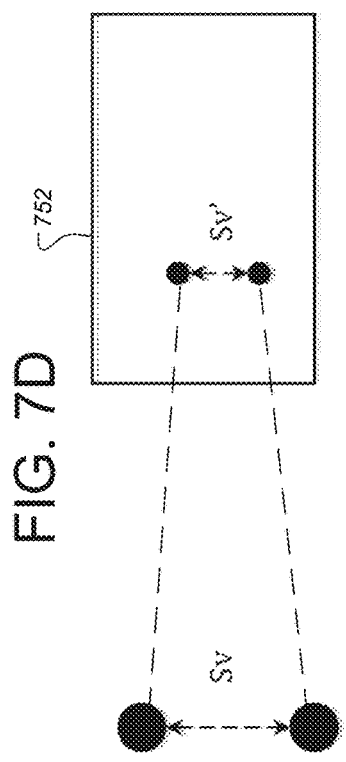
FIG. 7D
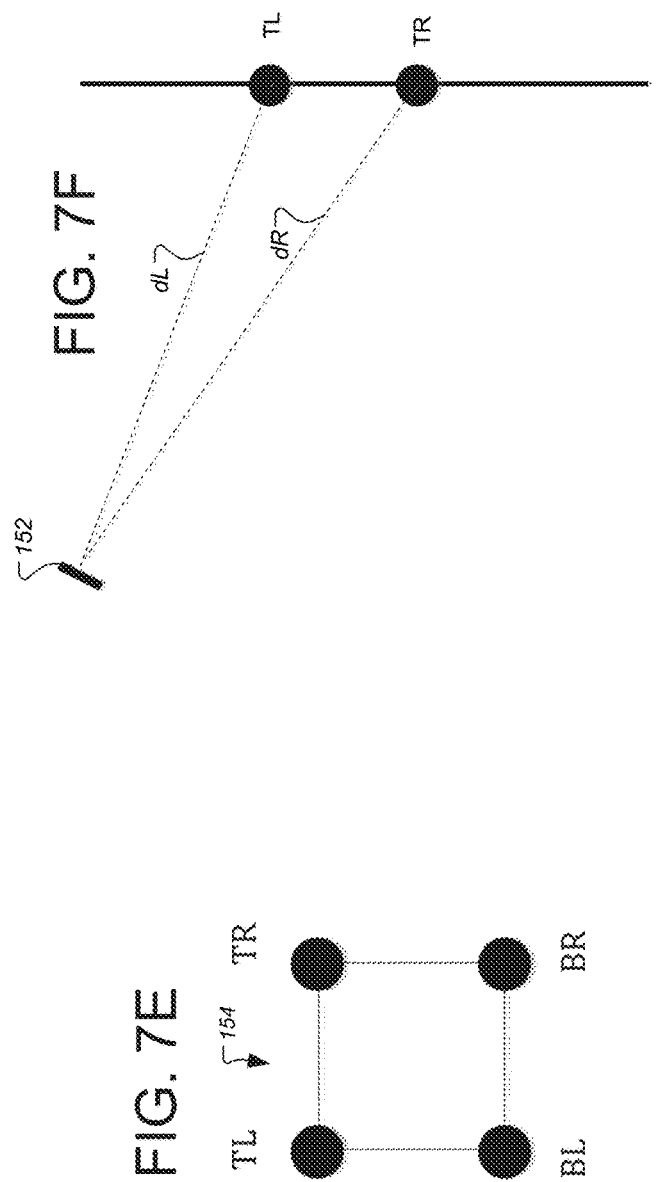
FIG. 7F
FIG. 7E

SYSTEM AND METHOD TO RESTRICT THE OPERATIONAL RANGE OF WIRELESS DEVICES

TECHNICAL FIELD OF THE INVENTION

The invention relates to wireless control systems for equipment used in facilities such as operating rooms, and more particularly, to safety systems for wireless control systems.

BACKGROUND OF THE INVENTION

As surgical and medical instruments grow in complexity, the control of the various instruments needed to conduct a surgery becomes more complex and costly in both personnel training and the surgical time needed to operate the equipment. In the late 20th century, state-of-the-art operating rooms included several electronic surgical instruments (e.g. electrosurgical units, insufflators, endoscopes, etc.). These instruments were separately operated by the surgeon and members of the surgical team. The industry improved upon this type of operating room by integrating the various instruments into a unified system. With this setup, the surgeon or members of the surgical team use a central controller ('room controller' or 'surgical control unit') to control many of the instruments through a single interface, preferably a graphical-user interface. Generally speaking, such central control units are built using modified personal computers, and the operating rooms that use them are commonly referred to as "digital operating rooms".

With the establishment of the digital operating room came the need for more portable, safe, and customizable remote control systems for operating room equipment. Although remote controls for surgical equipment are convenient and help maintain sterility, they have introduced certain heretofore unknown safety issues. One such safety issue is the problem of surgeons issuing commands into control devices that are mated inadvertently with a nearby room's surgical control unit. In that situation, a surgeon may attempt to control a surgical control unit present in the room they are occupying, only to inadvertently control another surgical control unit in a nearby room where an unrelated procedure is being performed. This problem is exacerbated by the fact that a surgeon may repeat commands in a vain attempt to operate the surgical control unit in the room they are occupying. This can result in injury to the patient and surgical team and/or damage to the equipment in the nearby room.

Various operating room remote control devices are known in the industry. For example, U.S. Pat. No. 8,175,590 shows portable remote control devices and a network of monitoring receivers that sense the presence of a remote control device and enable or disable the device. However, such systems require an extensive monitoring network to be installed and suffer from null zones where devices cannot be located. U.S. Publication No. 2011/0063429, commonly owned by the present applicant, describes a method of pairing a command microphone with equipment, and maintaining the pairing using confirmation sounds received by the microphone itself. Such systems are useful for pairing microphones but not useful for pairing other types of devices without a microphone. U.S. Pat. No. 7,463,813 shows a remote control device which is paired with medical equipment by a verification code. The code is then erased after a predetermined time interval to prevent inadvertent use of the controller. These types of systems suffer from potential user error and may inadvertently conclude a command authorization pairing during a procedure that takes longer than expected. Further, there is a tendency for personnel to avoid expiration by deliberately entering a procedure time above the actual time, which may lead to erroneous commands being issued. U.S. Publication No. 2009/0300507 shows an operating room remote control that is activated and deactivated by passing through an RFID portal at the door of the operating room. Such systems, however, are limited in that they require a single entry way to the operating area, and do not directly monitor the command device location on an ongoing basis.

There remains a need in the art for a safety system that prevents the inadvertent control of surgical control units with wireless command input devices.

SUMMARY OF THE INVENTION

It is an object of the invention to provide command device systems and methods which overcome the above-described problems and others associated with the use of remote control command devices, particularly in a medical environment, such as a surgical operating room environment. The invention encompasses methods of pairing a command device to a remotely controlled medical system. The invention also encompasses systems for remotely controlling one or more medical devices.

According to one aspect of the invention, a method is provided to pair a command device to a remotely controlled system, so that the command device may be used to control one or more medical devices of the remotely controlled system. The method includes providing a registration component at a designated location in an operating area such as an operating room. The registration component has a unique identifier associated with an operating area, and is used by bringing a portable command device within a designated proximity to the registration component. In response to an initiation input from the user, the method causes the command device to obtain the unique identifier from the registration component in a manner only allowed when the command device is present with the registration component. Next, the method sends a request from the command device to register for control of medical equipment in the operating area and associated with the registration component. While registered for control of medical equipment, the command device is able to transmit commands for controlling the medical equipment. The method also repeatedly estimates the location of the command device based on input from one or more sensors on the command device, and repeatedly checks the estimated location and in response to the estimated location being outside a designated area associated with the operating area, deregisters the command device from control of the medical equipment. The use of a registration component required to be sensed and verified by the command device which uses onboard sensors to track its location provides the advantage of an additional safety confirmation protocol, and improves the safety and usability of command devices over prior systems.

Some implementations of the method include determining an initial location for the command device relative to the registration component, and afterward estimating the location of the command device based on tracking movement relative to the determined initial location. In these implementations, determining an initial location for the command device may be done relative to one or more registration markers by recognizing at least one of the registration markers using a camera on the command device. The marker images may include a known shape from which a distance estimates is made by measuring the height or another dimension of the marker in terms of pixels on the device camera, or measuring distances between vertices of the shape to estimate the distance and angle of incidence between the camera and the marker image. After the initial location of the command device is determined, its current position may be tracked based on at least an onboard accelerometer of the command device. Determining an initial location for the command device may be done by determining the initial location relative to one or more registration components, or relative to a beacon LED arrangement positioned in the operating area using a camera on the command device, where the beacon LED arrangement includes multiple LEDs arranged in a known shape from which distance estimates are made by measuring distances between vertices of the known shape to estimate the distance and angle of incidence between the camera and the beacon LED arrangement.

Repeatedly estimating the location of the command device may be done based on at least data from an onboard accelerometer of the command device to track relative movement. Repeatedly estimating the location of the command device may also include determining the estimated locations relative to one or more beacon LED arrangements positioned in the operating area using a camera on the command device. In other implementations, repeatedly estimating the location of the command device includes determining the estimated locations relative to one or more marker images positioned in the operating area using one or more cameras on the command device.

Some implementations of the method may include checking whether the command device's estimated location is within a designated proximity of a respective medical device in the operating area, and if so updating a device control interface presented on the command device to present controls for the respective medical device.

In some implementations, repeatedly estimating the location of the command device further includes using data from multiple RF beacons in the operating area. Some implementations may also repeatedly estimate the location of the command device using signal strength data from one or more radio-frequency receivers of the command device, the signal strength data associated with one or more of designated transmitters in or near the operating area.

According to another aspect of the invention, a system is provided for pairing a command device to a remotely controlled medical system. The system includes a controller having a communications interface operable to control external medical devices. A registration component is also included, configured to store a unique identifier associated with an operating area. The registration component is also configured to display or broadcast the unique identifier. The system command device can communicate with the controller, and includes user interface, a processor, and sensors. The command device processor is programmed to cause at least one of the sensors to read or receive the unique identifier for the desired controller when placed within a designated proximity or physical relationship to the registration component, and programmed to receive commands entered at the user interface device and communicate the commands to the controller with the unique identifier. To maintain the registration, the command device detects with its sensors if it is removed from a designated area surrounding the controller. If the command device is moved too far, the controller 150 ceases sending commands from the command device to the medical devices.

In some implementations of the system, the command device repeatedly estimates its location using built in sensors, and if it leaves a designated area associated with the operating area, the system deregisters the command device from control of the medical equipment. The location estimates may be made using data from multiple RF beacons in the operating area. In some implementations, the command device determines its initial location relative to the registration component, and then repeatedly estimates its location based on tracking movement relative to the initial location. Determining the initial location may be done relative to one or more registration markers by recognizing at least one of the registration markers using a camera on the command device. In some implementations, repeatedly estimating the location of the command device further includes estimating the location based on an onboard accelerometer. Repeatedly estimating the location of the command device may be done by determining the estimated locations relative to beacon LED arrangements using cameras on the command device, the beacon LED arrangements including multiple LEDs arranged in a known shape from which the command device is programmed to make distance estimates by measuring distances on images captured at a command device camera. In some implementations, the registration component also includes beacon LED arrangements. In other implementations of the system, repeatedly estimating the location of the command device is done by estimating the location relative to marker images using the command device camera. The marker images include a known shape from which the command device can make distance estimates by measuring distances between vertices of the known shape, and then estimating the distance and angle of incidence between the camera and the marker image. The command device may also be programmed to check whether the estimated location is within a designated proximity of a respective medical device in the operating area, and if so, update a device control interface presented on the command device to present controls for the respective medical device.

These and other features of the invention will be apparent from the following description of the illustrative embodiments, considered along with the accompanying drawings.

BRIEF DESCRIPTION OF THE DRAWINGS

FIG. 6 depicts a partial perspective cutaway view of an operating area having a system in which visual location markers are placed at a designated height from the floor according to some embodiments.

FIGS. 7A-F are diagrams showing illustrative ways in which a command device camera is used to estimate location relative to a registration marker.

DESCRIPTION OF ILLUSTRATIVE EMBODIMENTS

Figure 1A:
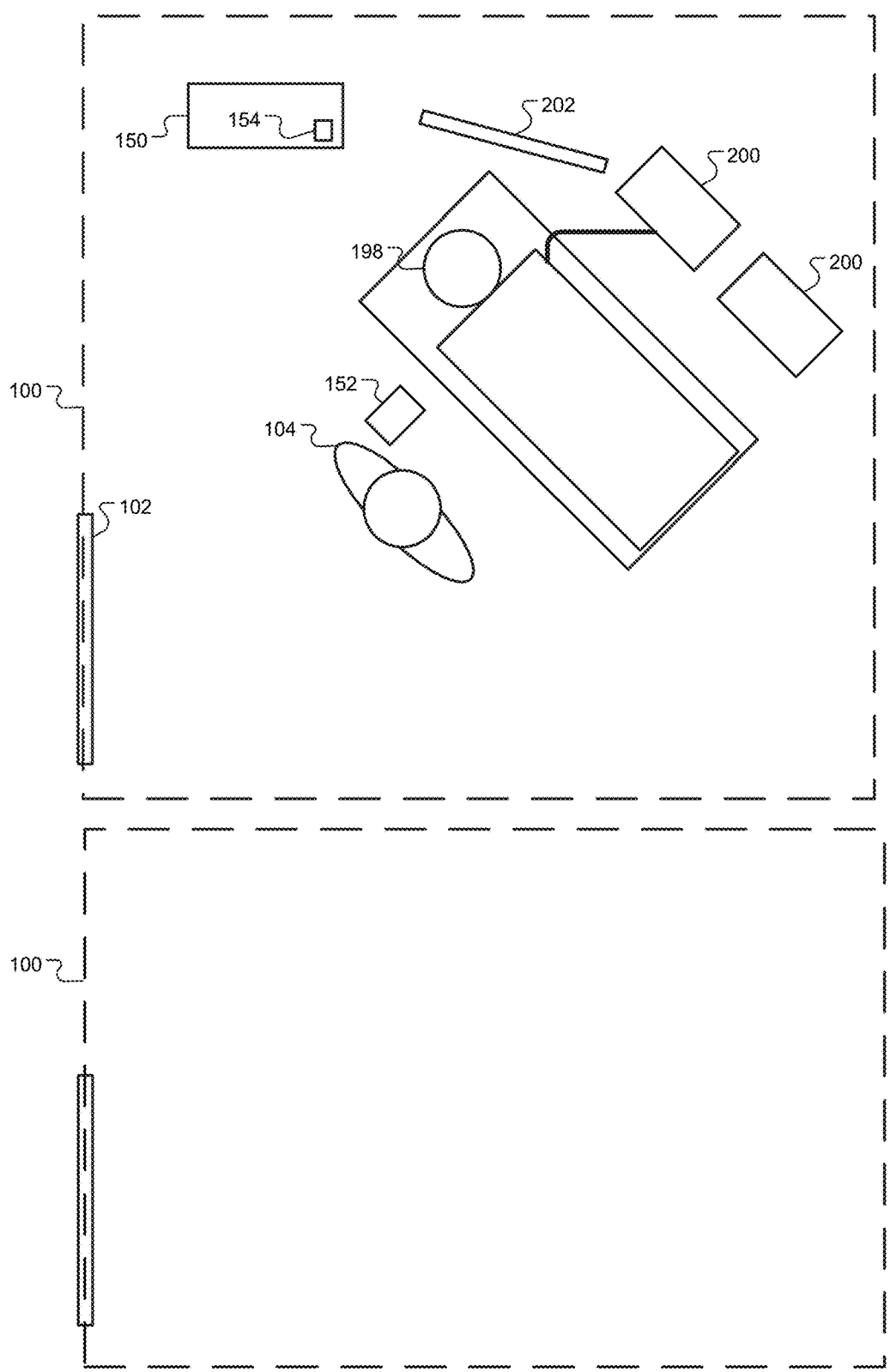
FIGS. 1A-B shows diagram representations of adjacent operating areas according to different embodiments.

The invention provides improved control systems and methods for safely controlling operating room equipment using remote controllers. FIG. 1A is a diagram view of two neighbouring areas 100, which may be an operating rooms, tents, curtained areas, or otherwise defined spaces for conducting surgical or medical operations, having one or more entries 102 which may be doors, gates, curtains, or other openings, or merely a demarcation of the entryway into a marked operating area. Each area 100 typically has patients 198, medical equipment 200, and control equipment such as controller 150, but only one operating area 100 is shown filled to simplify the drawing. Each operating area 100 is controlled by a controller 150, which communicates with command device 152, such as a wireless tablet or mobile control panel, to receive commands from an operator 104. The controller 150 validates commands and forwards them to the appropriate medical device 200. Controller 150 may in some cases process, translate, or interpret commands between different protocols employed to command the various medical equipment 200. Operator 104 issues commands via hand gestures, touch, or voice into command device 152 to control medical device 200 in the operating area 100. Associated with each operating area 100 are one or more registration components 154, which allow the command device to be safely linked exclusively to a single operating area to avoid transmitting commands into neighbouring operating areas 100, or otherwise interfering with equipment in other areas. The registration component 154 may be connected to the controller or placed elsewhere in the operating area, and may take on several different forms as further described below.

The controlled medical devices 200 are used to perform one or more medical procedures on patient 198. Digital commands are transmitted from command device 152 to controller 150. Controller 150 and/or control module 161 controls medical devices 200 by executing the commands. Usually, visual and audio feedback is given to operator 104 via display 202 and possibly additional sound feedback provided through speakers on the controller 150 or the various devices 200, or mounted at other locations in the operating area. Medical devices 200 may be any type of surgical device, bedside life support device, or any other medical device that can be controlled by controller 150. For example, medical device 200 may be an insufflator, a suction device, a light source, a video camera, a pressure gauge, a pump, an electrosurgical unit, a surgical table, a room camera, a room light, or an endoscope. Further, it is possible that multiple medical devices 200 will be operated by one controller 150 and any given command from operator 104 may be intended for one or more devices 200. While control of medical devices is described, other versions may perform command of other equipment types where safety of command device pairing is important.

In some versions, command device 152 is a tablet or has a graphical display, and is paired with controller 150 by operator 104 using software installed on command device 152 according to the processes described herein. For example, a user could press a button on tablet 152 or on its GUI, and begin a pairing process with controller 150 by scanning the registration component with the tablet camera, or activating a near-field communications link between the command device 152 and registration component 154, as further described below, to pair the command device with present controller 150 or operating area 100.

Some versions of command device 152 may include a microphone 112 coupled with a command device 152, such as a wireless tablet. In that case, command device 152 and a wireless headset must be paired with controller 150 in order for controller 150 to execute commands from those devices. While a wired microphone as such presents no risk of misdirected commands, even a short-range Bluetooth microphone has a signal strength that may reach into neighbouring operating areas and send commands to unintended locations. In some embodiments, a sound verification scheme may be used to pair a wireless microphone with a controller 150 or command device 152. Such a system is described, for example, in U.S. patent application Ser. No. 13/693,801, filed Dec. 4, 2012, titled "System and method for pairing a command device incorporating a microphone to a remotely controlled medical system," which said patent application is hereby incorporated by reference. With such a system, operator 104 can execute commands via command device 152 by first sending a command through the communication channels between tablet 152 and controller 150. Controller 150 will receive the command and verify it, and controller 150 will then execute the desired command and control medical device 200 as desired by operator 104.

Figure 1B:
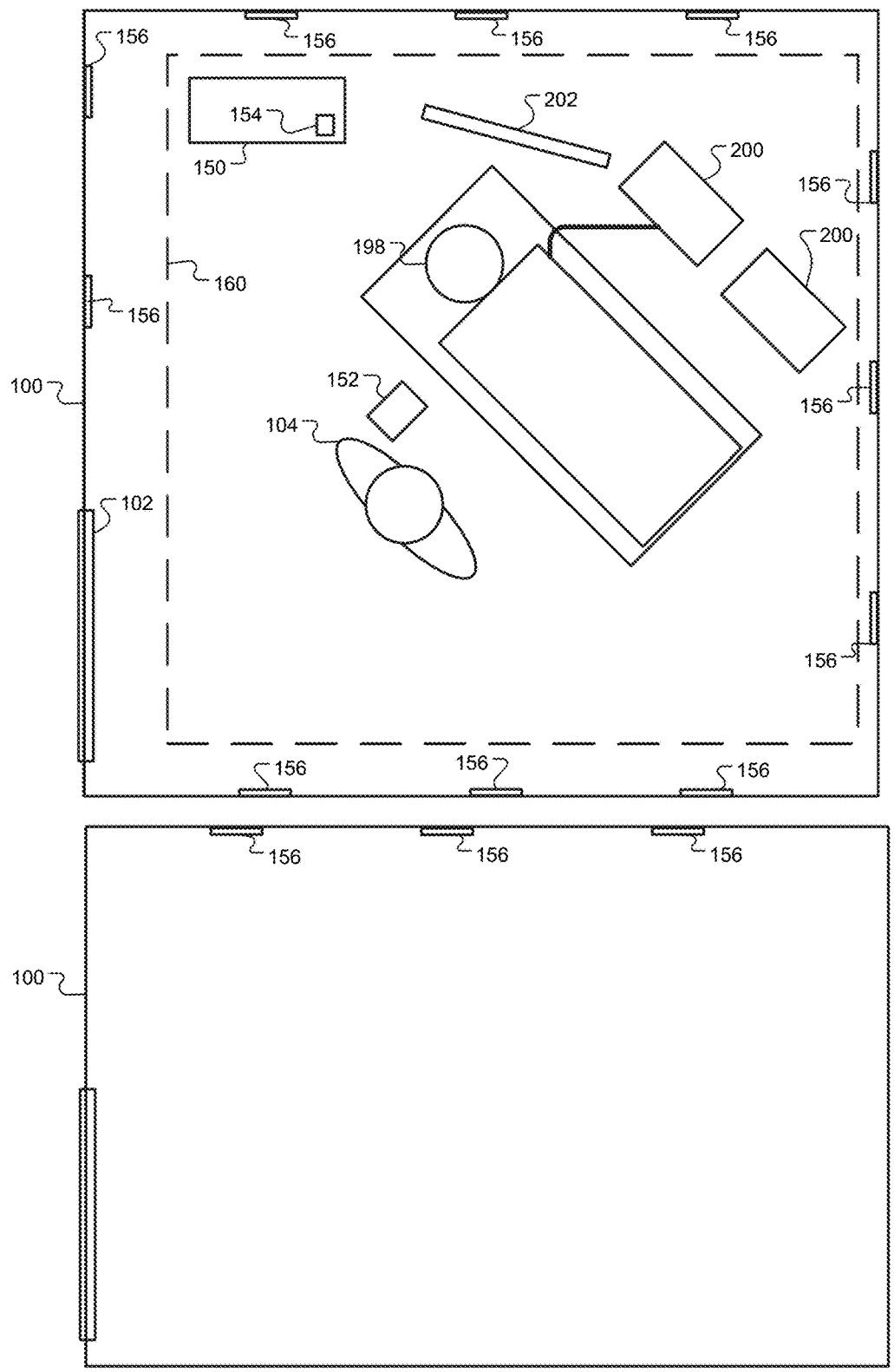

FIG. 1B is a diagram view of two neighbouring areas 100, in this embodiment having multiple locations markers or beacons 156 placed along the perimeter of the room, as will be further described below. While the upper depicted area 100 has multiple markers/beacons 156 placed along each edge, other embodiments (especially those employing RF beacons such as Bluetooth beacons) may use fewer markers/beacons 156, including a single beacon at each edge or corner, or beacons regularly positioned along the ceiling. Depicted as a dotted box is an example designated area 160 in which a command device 152 is allowed to move and remain registered in this example embodiment. While a box-shaped area is shown in this version, tracking schemes based on distance from a central point will have circular designated areas 160, and other schemes based on camera tracking of visual markers 156 may have their area 160 defined by the placement of markers 156 as further described below.

Figure 2:
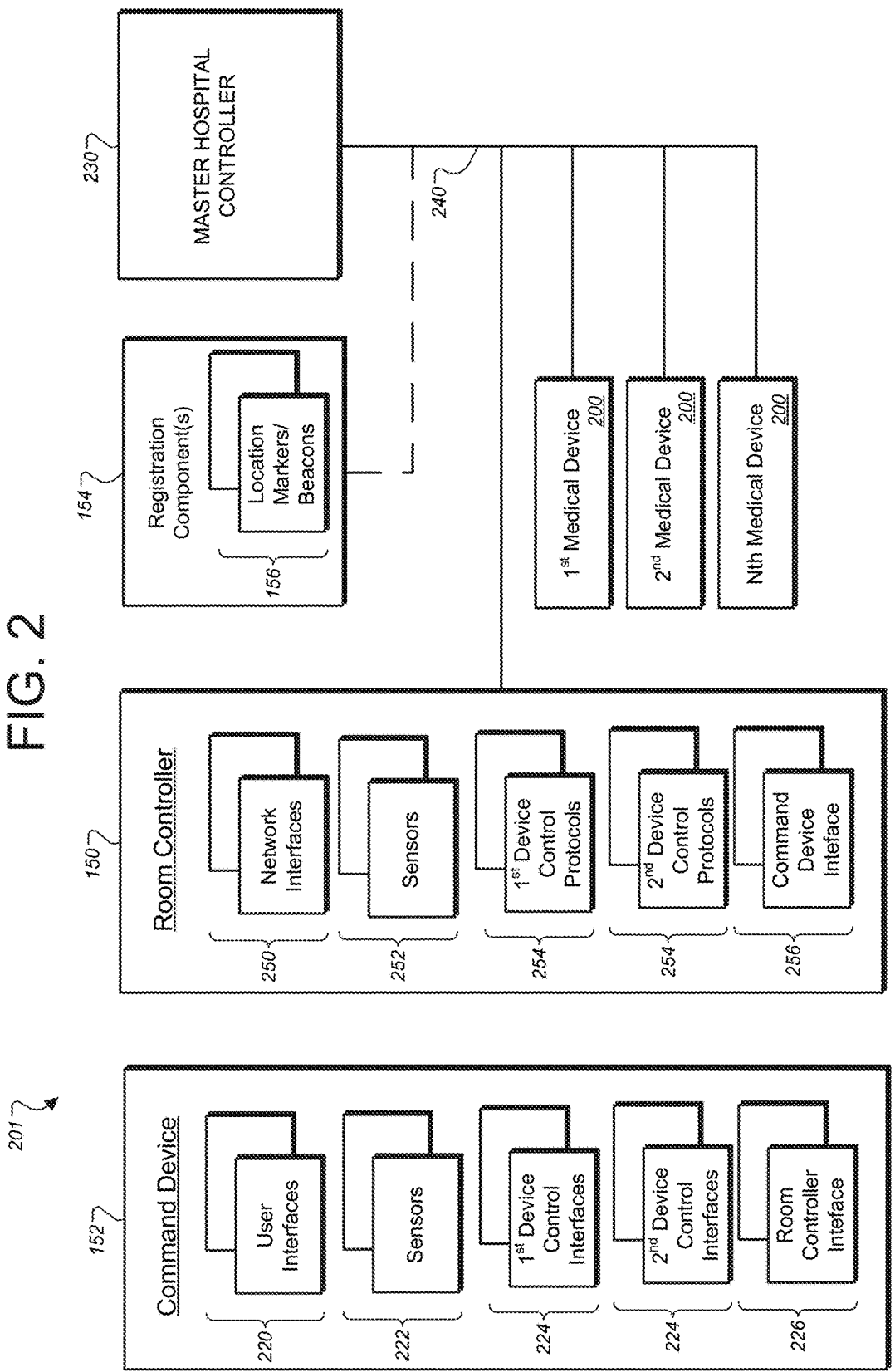
FIG. 2 is a block diagram of the system command and control devices according to some embodiments.

FIG. 2 shows a block diagram of command and control devices in a system 201 configured to control medical devices 200 according to an example embodiment. Generally, the control of devices in the room is accomplished by a system 201 including command device 152, room controller 150, registration component 154, and its associated beacons or markers 156 which may be integrated with registration component 154 or may be separately positioned.

Referring to room controller 150, this device may be entirely contained in single local piece of equipment, or may be connected through a network interface 250 to accomplish some of its processing and tracking functions by communication with a master server such as the depicted master hospital controller 230. In some cases, room controller 150 may have only a "thin client" architecture in which wireless communication to the command device 152 and the local medical devices 200 is accomplished through the room controller device 150 located in the operating area 100, and the remaining functions of the room controller, that is tracking registration, processing commands, equipment interface protocols, and logging are all performed at master controller 230 connected via a network 240 to control multiple operating areas. Also in some cases, some or all of the medical devices 200 may be connected to a network and receive their commands over the network 240, while in other cases the equipment may be connected by communications busses such as USB to controller 150 or by wireless or wired connections. In some embodiments, an indoor location server may be provided on network 240, which may be a separate server or integrated with master hospital controller 230 or room controller 150. The indoor location server provides an interface to define maps or other location definitions for the various operating areas, allowing an indoor positioning protocol to be employed by command devices 152. Generally such a server is employed with RF or visual light based embodiments, and provides ability to both define the map or layout of operating areas and specify the locations of markers or beacons 156 within the defined area. Such information is then used by command devices 152 in determining their location.

Room controller 150 preferably includes memory storing control protocols 254 allowing it to send commands to each device 200 which it is allowed to control. These may include standard medical command protocols or protocols specialized to each device. Some devices may have wireless control modules that are plugged into the room controller 150 allowing a direct connection, or wireless or wired network connection may be employed such as the depicted network 240. Room controller 150 also includes network interfaces which may be used to maintain the connection to command device 152, the medical devices 200, registration component 154, and the master hospital controller in those cases where a master controller is involved in tracking or managing operating room equipment. Room controller 150 may also include sensors 252 such as microphones, cameras, laser scanners, and NFC communications sensors. It should be noted that while preferred versions herein use a room controller configured to control all of the room equipment that has remote control capabilities, in some embodiments the techniques herein may be employed for remote control of less than all the devices in the room.

Figure 5A:
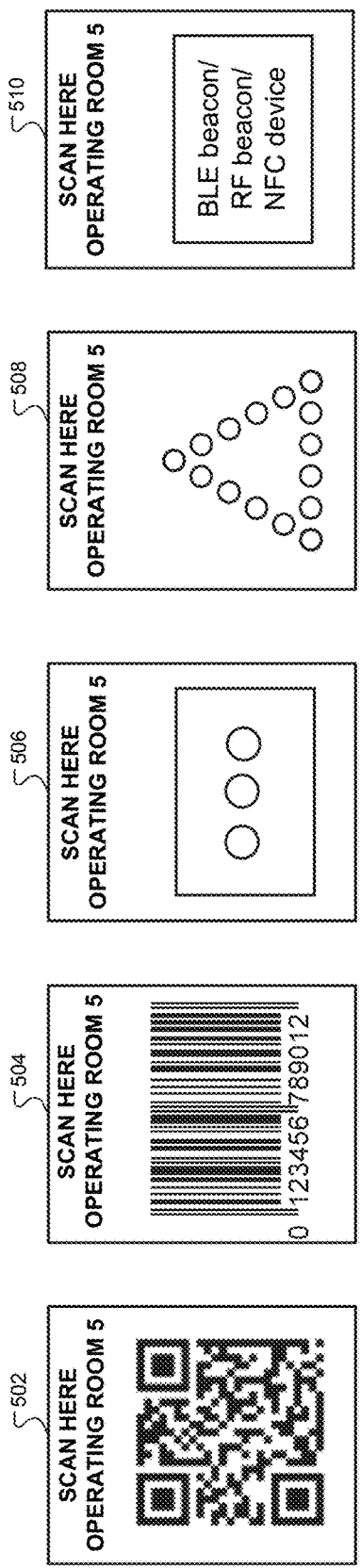
FIG. 5A is a diagram of several alternative registration components.

Referring still to FIG. 2, registration component 154 may be a device or passive marker, and is configured to store a unique identifier associated with an operating area, and to display or broadcast the unique identifier. Examples of such a registration component are depicted in FIG. 5A, where the depicted registration component 154 can take on several forms, such as a printed barcode 504, a QR (quick response) code 502, beacon LEDs 506 emitting unique light signals (such as signals distinguished by light color, or their flashing patterns, or identifiers and other data transmitted by visual light protocols), an LED arrangement 508, or a NFC device, or a Bluetooth Low Energy (BLE) beacon device or other low power radio frequency beacon 510, for example. Registration components and location markers may also be provided with a three dimensional structure allowing estimation of both distance and angle of incidence using a command device camera, such as the structure discussed with respect to FIG. 7C, having a marker protruding from the registration component. In some embodiments, both registration component 154 and location beacons 156 are embodied as LED beacons.

Figure 5B:
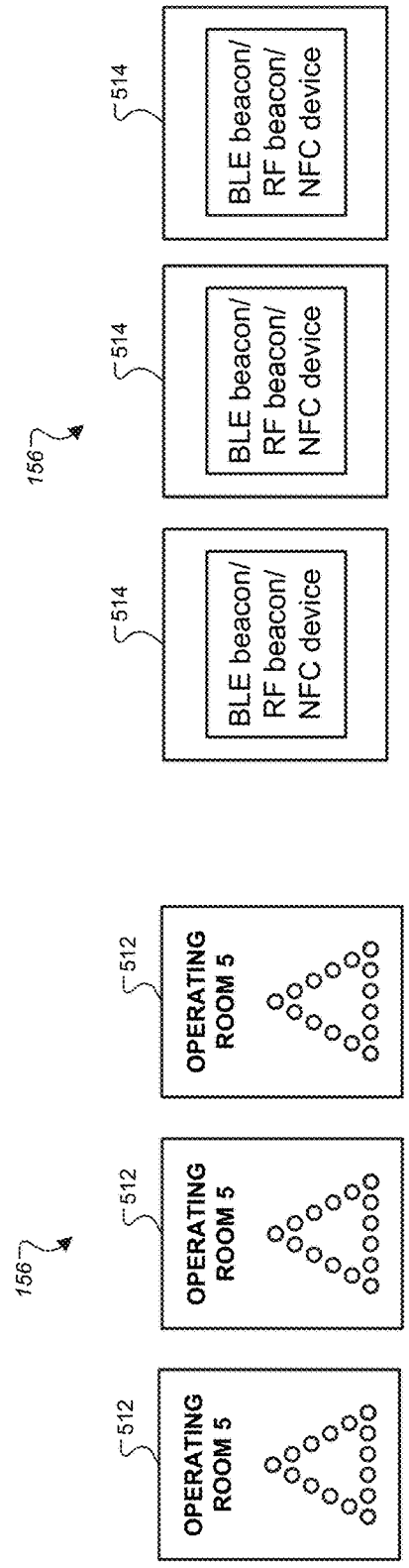
FIG. 5B is a diagram of some alternative sets of location markers or beacons.

FIG. 5B shows two different examples of location markers or location beacons 156 according to different embodiments of the present invention. The depicted beacons 156 are typically used in a group of similar beacons, which may be identical, or may have unique identifiers and having recorded locations such that the command device can estimate its location from the beacons identifier(s) received. Depicted are a group of LED beacons 512, which are placed around operating area 100 in locations such as those depicted in FIG. 1A. In some versions, such beacons are identified by the shape of the LED arrangement therein, such as the depicted triangle. In one version the location beacons 156 include a known shape or pattern is embodied in LED beacons or a printed marker, the known shape having straight sides that have known angles at their vertices, allowing for image recognition and relative measurement of shape sides and vertices. Preferably the shape is asymmetric vertically so that its orientation may be determined by image recognition. A registration component 154 may also include a similar known shape, printed or in an LED arrangement. In some versions, the LED beacons provide indoor location services by broadcasting with visible light or infrared, using on-off keying (OOK), amplitude-shift keying (ASK), or digital pulse recognition (DPR), which broadcasts pulses designed to work with a mobile device camera shutter and array readout process to convey the desired data into the images captured on the mobile device camera. Using these or other suitable techniques, an LED-based registration component or location beacon may broadcast or display an identifier unique to the operating area as well as a location identifier or other data specifying the location of the registration component 154 or location beacon 156. Preferably, the registration component 154 is attached or placed at a designated location in the operating area, preferably a central location such as on or near the operating table. Also shown in FIG. 5B is an example group of location beacons 156 embodied as RF beacons or transmitters 514. In these embodiments, the location beacons 156 include one or more, and preferably at least two or three, RF beacons that broadcast a unique identifier associated with the operating area 100 or the location of the operating area 100. Location beacons 156 may be Bluetooth low energy devices, NFC devices (which at low frequencies such as at or near 30 MHz may extend the use of near-field effects using near field electromagnetic ranging (NFER) to a range of many meters with a location resolution of about 1 ft), or other RF beacons such as wi-fi base stations, cellular micro-bases, or other wireless networking base stations. In some cases, the registration component 154 or location markers/beacons 156 may be connected to a network 240.

Referring again to FIG. 2, the depicted system 201 also includes the command device 152, which is operable to be in communication with the controller. The command device includes a user interface device such as a touchscreen display or a voice command interface, a processor operably coupled to the user interface device, and one or more sensors 222 operably coupled to the processor. The command device processor is programmed with software and drivers to provide functionality for the various depicted subsystems. While a tablet is preferred, other interfaces such as advanced heads-up displays projected from user headwear or glasses may be used. In some cases, the command device 152 may include multiple physical devices. A user interface may be separated from the sensors but function as a combined unit, such as, for example, when a head-mounted projection display such as glasses or a holographic projector is used to provide the interfaces 220, 224, and 226, while the sensors 222 may reside in a processing module worn on the belt or a strap or pocket of the person wearing such a command device 152. The headgear and processing module are preferably connected by a wired bus but may be connected with a secured wireless link.

As further described below, command device 152 is programmed to cause at least one of the sensors to read or receive the unique identifier when placed within a designated proximity or physical relationship to the registration component 154, and programmed to receive commands entered at the user interface device and communicate the commands to room controller 150 with the unique identifier. Command device 152 is further programmed to detect with at least one of the sensors 222 when command device 152 is removed from a designated area surrounding the controller 150, and in response, the system cease sending commands from command device 152 to the one or more external medical devices 200. The command device 152 subcomponents in this example embodiment include one or more user interfaces 220 such as input buttons, which may be mechanical or presented on the touchscreen display, and a microphone interface which may all be used to receive user commands. The depicted functional blocks of command device 152 are preferably implemented with a commercial tablet computer having a standard hardware configurations and customized software, but may also include customized hardware, or a tablet with added customized accessories, such as, for example, a NFC communications device, or a specialized IPS (indoor positioning system) receiver or transceiver which may be added to the tablet as a plug in accessory or powered case accessory, for example. Sensors 222 on command device 152 provide ability to sense and track, or at least estimate, the location of command device 152 inside the operating area, providing a safety feature to allow location-based de-registration, or unpairing, by the command device 152 when it leaves the operating area, preventing issuance of commands from command device 152 to the wrong medical equipment 200, such as equipment in a neighbouring room, as further described below. Typically, the use of a registration component allows accurate pairing of command devices, and therefore the highest risk of erroneous commands comes after the procedure is over, or if the command device is removed from the operating area, and someone attempts to use the command device in another operating area while it is still paired with the previous room controller. The use of a registration component and automatic deregistration procedures as described herein helps mitigate this user error risk. Command device 152 further includes device control interfaces 224 for each medical device 200 for which it is able to present a menu, button, or other control interface. These interfaces may be communicated by the room controller 150 to the command device 152 so as to manage the display and user interfaces of command device 152, or may be held in the software programming of command device 152. A room controller interface 226 allows the user to both initiate the pairing process described below, and to manage the functions of room controller 150 through the command device 152 after the devices are paired. It is noted that the room controller interface 226 may also include functionality that tracks or registers the location of the medical devices 200 and causes command device 152 to present the appropriate control interface 224 when it is moved within a designated proximity to a particular medical device 200. The use of a registration component required to be sensed and verified by the command device, integrated with location tracking by the command device itself using onboard sensors relative to the location markers, provides additional safety confirmation protocol improving the safety and usability of wireless command devices over prior systems.

As with the room controller, a single device or selected group of devices may be controlled by a particular command device 152, such as surgical equipment operated by a special sub-team, or any other desired grouping of equipment. For complex procedures in which the surgical team includes multiple specialties, for example, more than one command device 152 may be used. Also, while equipment is typically configured to be controlled by only one controller at a time, in some cases multiple controllers may direct the same equipment. Such cases typically require an explicit authorization to register both command devices 152 to avoid conflicting or otherwise detrimental overlap of commands. In use, the command device 152 serves to track its own location with respect to the operating area to help manage the pairing with room controller.

Figure 3A:
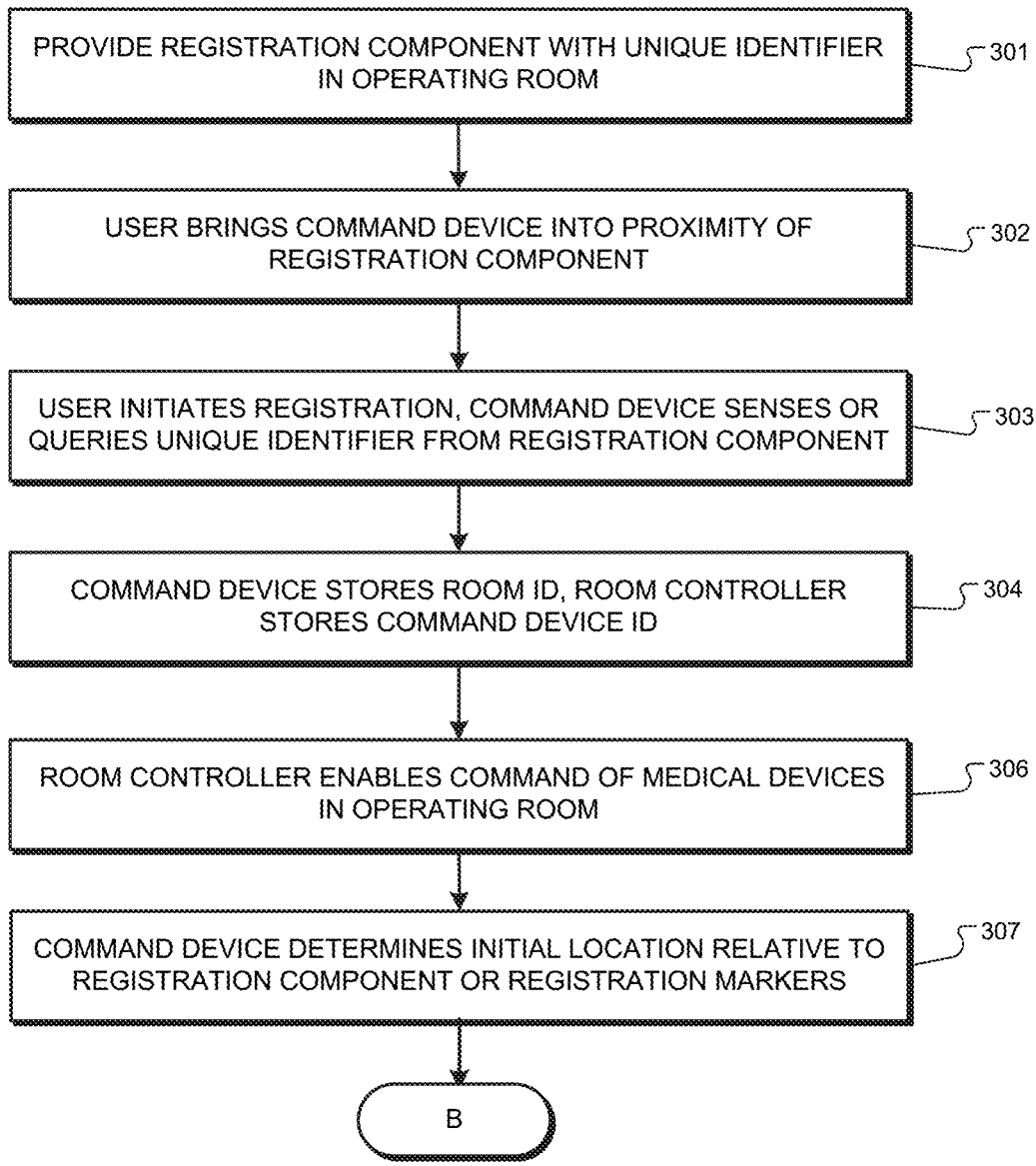
FIGS. 3A-B show a flowchart of a process for pairing and tracking a command device for use in a particular operating area according to one embodiment.
Figure 3B:
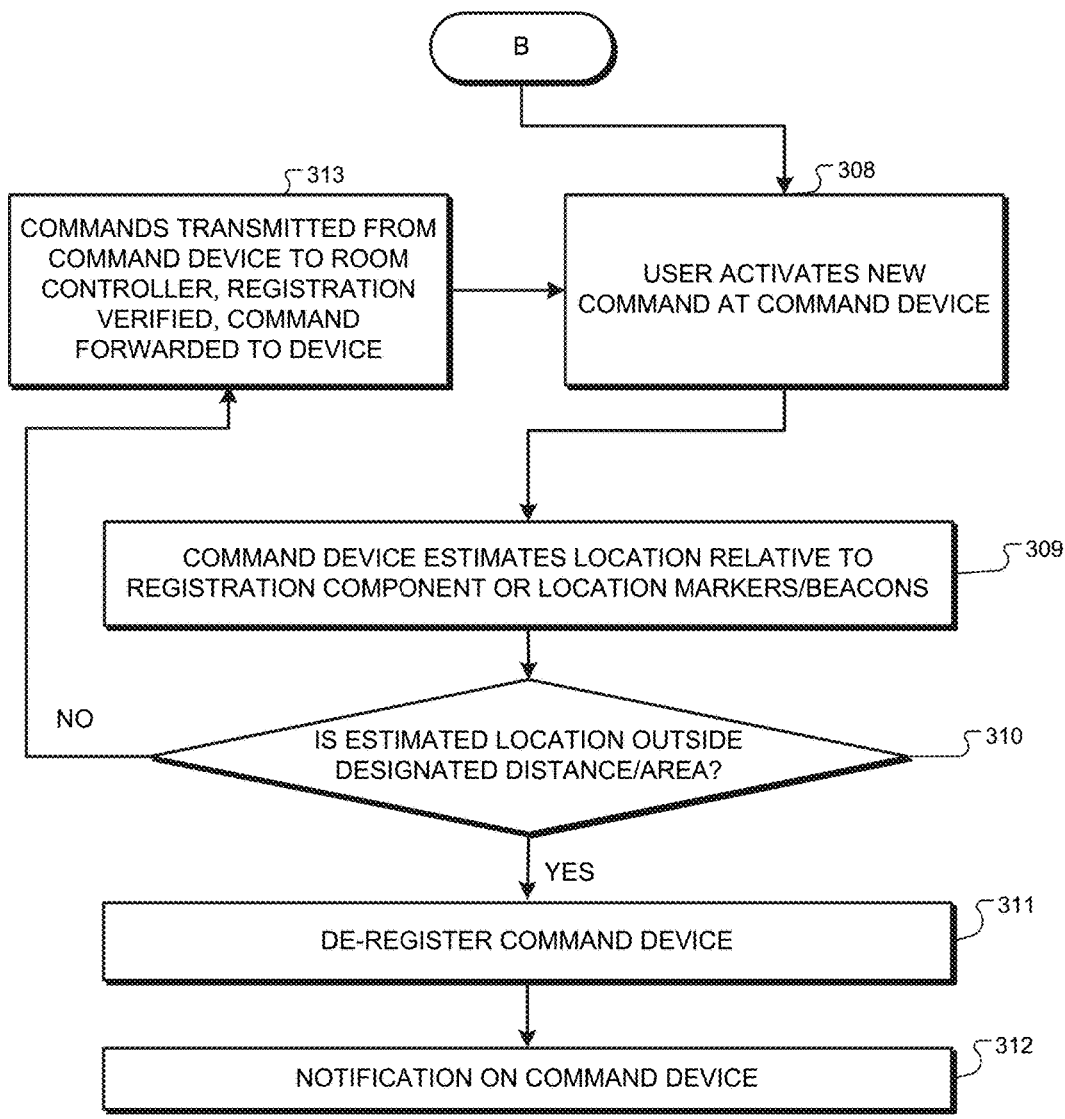

FIGS. 3A-B show a flowchart of a process for pairing (registering) and tracking a command device 152 for use in a particular operating area. A preferred process will now be described with reference to the functional blocks of FIG. 2 and the process of FIGS. 3A-B. The depicted process of FIGS. 3A-B begins at block 301, which provides a registration component 154 at a designated location in an operating area 100, the registration component 154 having a unique identifier associated with an operating area 100. Registration component 154 is typically provided at a fixed location in the operating area 100, which location may be known or designated to the system, but registration component 154 may in some cases be moved such as being attached to an operating table or a rack carrying room controller 150. At block 302, the user brings a portable command device 152 within a designated proximity to the registration component 154, and causes the command device to obtain the unique identifier from the registration component in a manner only allowed within the designated proximity. This step may be initiated automatically by the command device in response to being brought within the designated proximity to registration component 154, or may be in response to an input from the user as shown at block 303. The initiation may involve a touch or near-touch of an NFC sensor, or scanning a QR code, bar code, or LED beacon with the command device camera, for example. The designated proximity may be inherent to the method used to obtain the identifier from registration component 154, or may be set by the system designer or administrator. Preferably, the designated proximity of command device 152 to registration component 154 is set to much less than the size of operating area 100, requiring that the command device be inside the operating area to be registered for control.

Next at block 304, the process includes sending a request from the command device 152 to register for control of medical equipment in the operating area and associated with the registration component. This request may be sent directly from the command device 152 to the room controller 150 through a wireless link, or may be sent over a network. In a preferred version, a wireless network connection is used, with command device 152 and room controller 150 both being connected to the network. In some versions, command device 152 may use the unique identifier to look up or request an IP address or other address for the local room controller 150, and in other versions the IP address may be included in the unique identifier or a data payload attached therewith. A lookup may be made in memory of the command device 152, or may be made by a request over the network 240 for a master controller 230 to provide the address of the local room controller 150. In other versions, the unique identifier allows command device 152 to establish a direct connection to room controller 150, for example by directly or indirectly providing a Bluetooth address and/or login credentials. Preferably the registration process uses an exchange of ID data both ways, as reflected at block 304, where the command device 152 stores the room controller ID, and the room controller 150 stores the command device ID. This causes initialization of a registration state in which the command device 152 is authorized to send commands for the medical devices 200 associated with the room controller 150 at block 306.

With the command device 152 registered, it becomes necessary to track its location, on an ongoing basis, accurately enough to determine that the command device 152 is still in the operating area 100 for which it is registered. The registration may involve an initial location check as well, also using sensors on board command device 152. In the version of FIGS. 3A-B, the location tracking involves the command device determining its initial location relative to the registration component 154 or one or more registration markers or beacons 156 provided in the operating area 100. For embodiments in which the determination at block 307 is done by recognizing that control device 152 is at the designated physical proximity to registration component 154 required for registration, the location of registration component 154 may be used as the initial location. Other versions may use sensors on the command device 152 to sense data such as visual data, LED or infrared LED beacon data, or RF data to determine the initial location.

After block 307, the flowchart goes to the B marker on FIG. 3B where the command device is in a registered state in which it is allowed to pass commands through controller 150 to the equipment 200. In the depicted version, the user enters a command at block 308, and in response the command device performs a location estimate at block 309. Next, the process checks the command device location to see if it outside the designated distance or area at block 310 before any command is transmitted from command device at block 313. It is noted that the room controller typically verifies the device ID and registration at block 313 in addition to the location checking performed by the command device. From block 313, the process then waits for more user command activations at block 308. While the flowchart shows a loop, the actual process may be interrupt driven and may include additional location estimates by the command device besides those done in response to user commands. Further, a background process may update the location estimates when the device is moved, and therefore block 309 may be skipped and the current location estimate used for the comparison at block 310. Preferably, as long as command device 152 remains in the registered state to pass commands, typically for the length of a medical procedure or for an entire day's set of procedures in the same operating room or operating area, command device 152 continues to estimate its own location in the operating area 100, as shown at block 309, and then at block 310 checks if the estimated location is outside the allowed area, such as area 160 in FIG. 1B, or is outside of a designated distance from the registration component or another selected location such as the center of the operating area. This tracking essentially determines whether command device 152 has been removed from the operating area, but may or may not employ the exact boundaries of operating area 100. The estimated location at block 309 may employ a variety of sensors, or combination of sensor readings, of sensor devices integrated with or connected to command device 152. In one embodiment, an accelerometer is used to track the movement of command device 152 from the initial position. For location estimates that are not in response to a user command, a background process may also perform the repeated location estimate of block 309, or it may be performed on an interrupt fashion based on sensor input indicating that command device 152 has moved. In one simple embodiment of the steps shown at 308, 309, and 310, the device checks for sensor 222 input showing a marker or LED beacon 156 with indicating the device is located in the proper operating area before sending a command.

As long as the location tracking at block 310 determines that command device 152 is within the allowed area, the process returns to block 308 were more commands may be issued. If, at block 310, the process finds that command device 152 is outside of the designated area, the process goes to block 311 where it de-registers the command device 152, or unpairs it from the room controller 150. Then, at block 312, the process displays a notification on the command device to confirm that the command mode is being stopped. Other versions may provide a prompt requesting the user to confirm before de-registering the device. However, to better mitigate the hazards of users not following the proper procedure, it is better to automatically de-register and provide a notice. After such de-registration, the user must again start the registration process (block 302) to enable commands again.

Figure 4A:
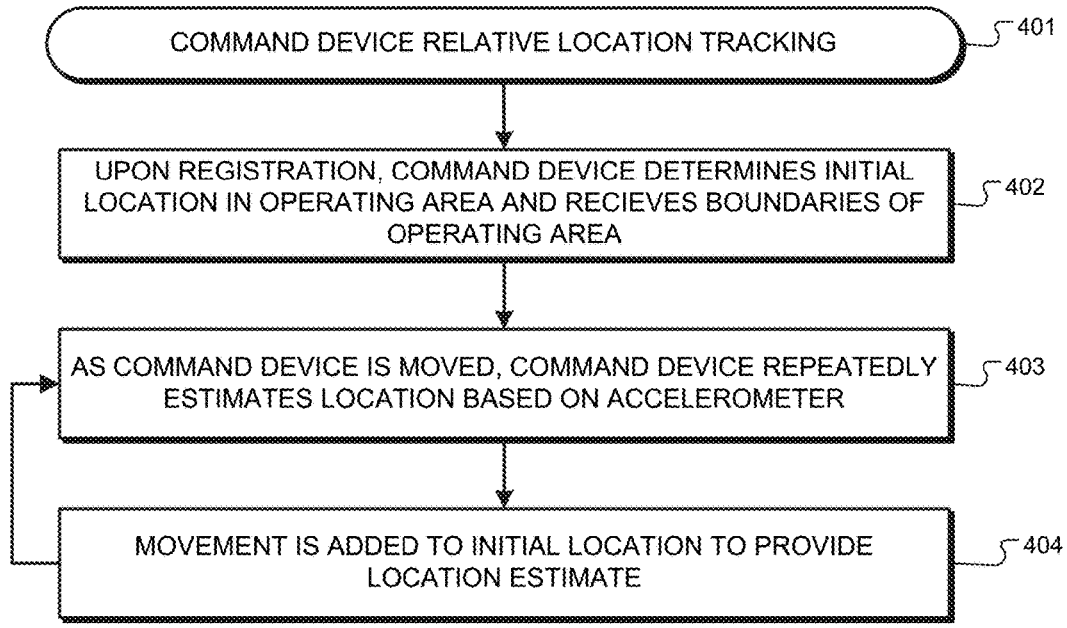
FIG. 4A shows a more detailed flowchart of a process for tracking relative location of a command device from an initial position.

FIG. 4A shows a more detailed flowchart of a process for tracking relative location of a command device from an initial position. The process in this version includes repeatedly estimating the location of the command device based on tracking movement relative to the determined initial location of the command device, and begins at block 401 in the depicted flowchart. The process is one embodiment of the location estimating process used in FIGS. 3A-B, and is generally initiated upon registration of the command device 152 with a room controller 150. At block 402, the command device 152 determines its initial location within the operating area, in the manner described above, such as by employing a known location of the registration component or by user pointing device camera toward one or more location markers or beacons 156 located within the operating area 100. In the simplest embodiment of this step, command device 152 simply determines from a sensor detecting presence of a marker/beacon 156, that the device is inside the operating area 100, without further location resolution. Such a case is typically accomplished with a visual marker or LED beacon/marker arrangement such as 502, 512, 504, 506, 508 depicted in FIG. 5A, in which the marker or LED signal is accessible to the command device sensors 222 only inside the operating area. The process may also involve placing the command device in a specified location and requiring a user input to initialize the location tracking.

Next, at block 403, as the command device 152 is moved around the operating area 100, or out of the operating area 100, the device 152 repeatedly estimates its location based on at least data from an onboard accelerometer. Data from a gyroscope may also be used or a combined orientation and acceleration sensor. The pose (orientation of the command device) is typically necessary to interpret acceleration data. Pose may be tracked by using electronic gyroscope sensors on the command device, the tracking managed by a background process and may also be estimated from a camera image of a location marker 156, if the marker has a shape from which its orientation can be determined. In some versions, repeatedly estimating the location of the command device 152 includes determining the estimated locations relative to one or more LED beacon arrangements or location markers 156 positioned in the operating area 100 using one or more cameras on the command device 152, the one or more beacon LED arrangements including multiple LEDs arranged in a known shape from which distance estimates are made by measuring distances between vertices of the known shape to estimate the distance and angle of incidence between the camera and the beacon LED arrangement. An example of such beacon arrangements 156 are depicted in FIG. 6. In FIG. 4A, at block 404, the determined movement is added to the original location to provide an estimated location relative to the original determined location.

Figure 4B:
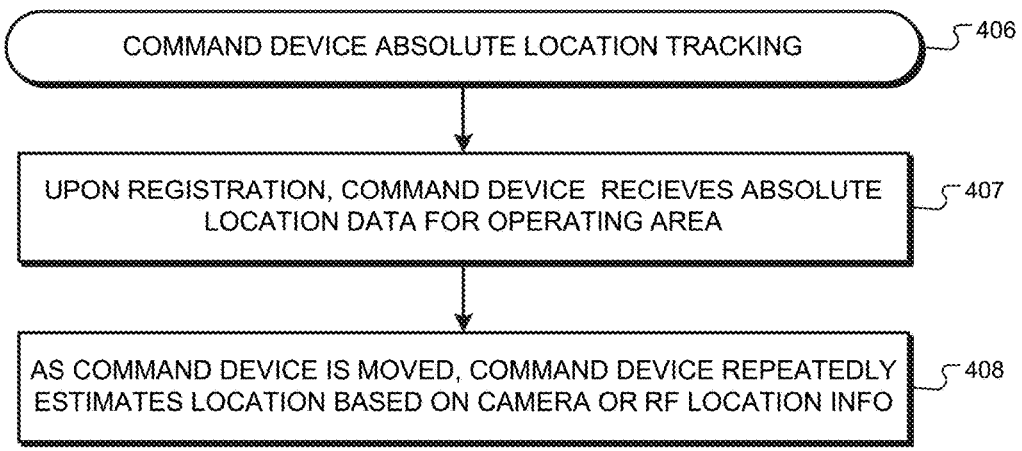
FIG. 4B shows a more detailed flowchart of a process for tracking location based on the absolute position of the command device.

FIG. 4B shows a more detailed flowchart of a process for tracking location based on the absolute position of the command device 152. The process begins at block 406, which is started upon registration of the command device 152 with a room controller 150, creates location estimates based on tracking the absolute position of the command device using sensors on the command device. Next at block 407, the process receives location data indicating the boundaries or center of the operating area. In some versions, such data may be sent to the command device 152. In other versions, the data may be stored at the room controller 150. At block 408, in some versions, repeatedly estimating the location of the command device 152 includes determining the estimated locations relative to one or more LED beacon arrangements or location markers 156 positioned in the operating area 100 using one or more cameras on the command device 152, the one or more beacon LED arrangements including multiple LEDs arranged in a known shape from which distance estimates are made by measuring distances between vertices of the known shape to estimate the distance and angle of incidence between the camera and the beacon LED arrangement. In some versions, repeatedly estimating the absolute location of the command device 152 may involve repeatedly determining the signal strength of a designated RF signal such as that from multiple Bluetooth beacons, associated with the room controller 150. In the simplest version, a single one of such beacons may be placed, for example, directly connected to the room controller 150, or at a fixed location such as, for example, the center of the operating room attached to a light, or operating table, or other suitable location. In such case, the decision at block 310 (FIG. 3B) will involve estimating the command device's distance from the beacon. Technology such as Bluetooth proximity sensing may be employed to provide an estimated distance from such a fixed location beacon. A more complex version may employ multiple Bluetooth beacons configured to provide interior positioning data by being positioned around the walls or boundaries of the operating area, such as the beacons 156 depicted in FIG. 1B. In such case, a map of the operating room may be provided upon activation designating the area in which the command device is allowed to command the medical equipment 200, and the command device may track its location on the map and check if it is outside the designated area before sending each commands. Other embodiments include repeatedly estimating the location of the command device using signal strength data from one or more radio-frequency receiver of the command device, the signal strength data associated with one or more of designated transmitters in or near the operating area, the transmitters identified to the command device as part of the registration process at block 407.

In other embodiments, repeatedly estimating the location of the command device 152 includes determining the estimated locations relative to one or more marker images positioned in the operating area using one or more cameras on the command device. The one or more marker images including a known shape from which distance estimates are made by measuring distances between vertices of the known shape to estimate the distance and angle of incidence between the camera and the marker image.

It is noted that while FIGS. 4A-B show using accelerometer or a device camera or RF receiver as an onboard sensor on the device, other versions may use a combination of these tracking methods. In such cases, if any tracking method indicates that the command device 152 has left its registered operating area, the process of block 311 may be activated and the device de-registered. In some embodiments, the process may also include repeatedly checking whether the estimated location is within a designated proximity of a respective medical device in the operating area, and if so updating a device control interface presented on the command device to present controls for the respective medical device.

FIG. 6 depicts a partial perspective cutaway view of an operating area having a system in which visual markers are placed at a designated height along the boundaries of the operating area. The depicted visual markers 156 are preferably any of the types of visually based markers described herein. Preferably they are placed at a height H that is the average chest height of 115 cm-130 cm, or within 10 cm of such height. A system with visual markers such as a pattern or shape requiring a command device camera to observe the shape may involve the user holding the device with the camera pointed substantially horizontally. The depicted scheme is merely one example, and other schemes may be used that involve markers or beacons observable only within a designated operating area. A registration component may also be embodied as a marker placed as shown.

Figure 7C:
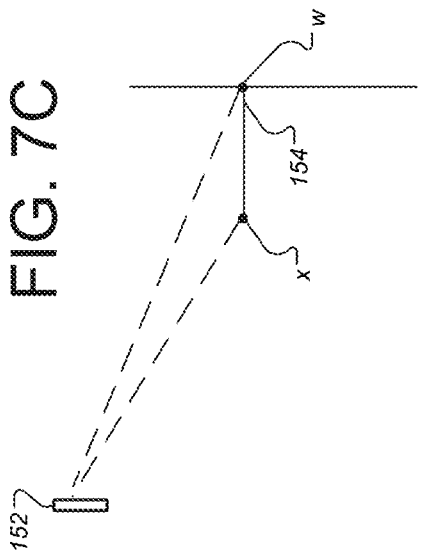
Figure 7B:
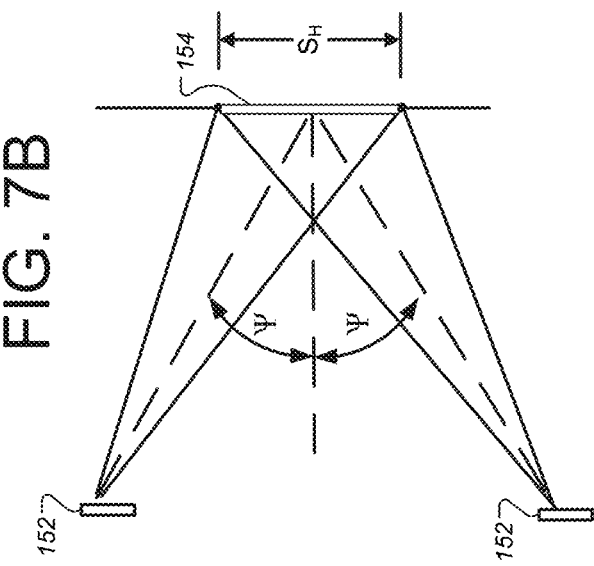
Figure 7A:
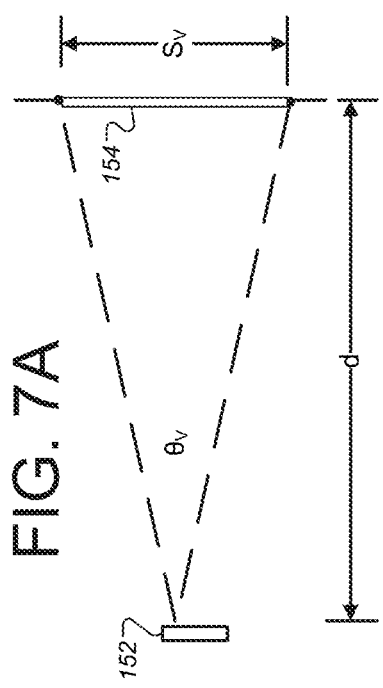

FIG. 7A is a diagram of a side view of the command device and registration component when estimating the initial position of the command device. To estimate the initial position of the command device from a registration component 154, an assumption is made that the elevation of the command device is approximately that of the registration component. However, if the command device is positioned at a higher or lower elevation relative to the registration component, the corresponding distance estimation error will result in an overestimation of the distance to the registration component, practically reducing the allowed range of motion of the command device. The same assumption may be used when repeatedly estimating the command device's position.

As depicted in FIG. 7D, when attempting to register the command device, an image of registration component 154 is captured by the onboard camera, which has known focal length, sensor size and sensor resolution. The registration component is made of a set of markers organized in a pattern with distance Sv between two vertices (markers), the markers preferably easily distinguishable from each other with image recognition. Within the image of the registration component captured by the command device camera, the distance or dimension Sv' as seen on the command device image sensor 752 can be measured between the markers. The measurement involves two steps: first identify the pattern of markers on the picture corresponding to the vertices of the registration component, then determine the two-dimensional coordinates of the markers on the picture and the distance Sv' between them. The physical distance 'd' (FIG. 7A) between the command device and the registration component is inversely correlated to the distance Sv' between the markers as measured on the image: the smaller the measured distance Sv', the greater the distance d between the command device and the registration component. The distance d between the command device and the registration component can then be determined through an appropriate lookup table, or calculated according to the imaging sensor characteristics (resolution, sensor size) and optical characteristics of the camera (focal length).

FIG. 7B is a diagram of a top view of the command device and registration component showing different angles of view that may occur. The horizontal distance between registration component vertices is shown as $S_H$. In some versions, to estimate the exact spatial position of command device 152, a registration component organized as a pattern of markers arranged in a square pattern is used, such as that depicted FIG. 7E. The depicted makers are labelled according to their position (i.e. TL is top-left), and are preferably visually distinguishable from each other in a way easily recognizable with image recognition. This registration component may be recognized and processed by the command device camera as depicted in FIG. 7F. Assuming that the command device is roughly vertically aligned with the registration component, the distance dL (FIG. 7F) can be estimated as indicated above by measuring the distance between the images of markers TL and BL (FIG. 7E). Similarly, distance dR can be estimated by measuring the distance between the images of markers TR and BR. The known spatial position of TL and the distance dL identify a circle centered on TL, resting on the horizontal plane identified by TL and the command device (because of the assumption that the command device is at the same height as the registration component, there is always an horizontal plane intersecting these two points), and crossing the command device 152. Similarly, TR and dR identify a second circle resting on the same horizontal plane. The intersection of the two circles uniquely identifies the coordinates of the command device on the horizontal plane. It should be noted that it is not strictly necessary to have a registration component that is either symmetric or partially aligned either vertically nor horizontally. Also, to a certain degree, rotation or tilt of the command device with respect to the vertical and/or horizontal axis can be compensated for. For example, in a normal use case where a user holds the command device roughly at chest height, any tilt cannot exceed a certain angle or the registration component will be outside the camera's field of view. The software on the command device can instruct the user to center it so that the registration component appears roughly in the center of the frame. Rotation can be compensated for since the orientation of the registration component is known. Further, the accuracy of the estimation can be improved by increasing the separation of the markers on the registration component.

As seen in FIG. 7B, if command device 152 is not directly in front of registration component 154 (i.e. the bearing angle is not equal to 0) the command device may lie on either the left or the right of the registration component. An alternative method of determining the side on which the command device lies is depicted in the diagram of FIG. 7C. This technique employs a distinguished marker (x) protruding from the registration component from the position of another marker (w) on the wall, as shown in FIG. 7C. Both markers are distinguishable by image recognition through the command device camera, such as by having different shapes, markings, colors, or relative sizes. If the command device is to the left of the registration component the protruding marker (x) will appear to the right of marker (w) when viewed from the command device camera. Similarly, if the command device is to the right of the registration component the protruding marker (x) will appear to the left of marker (w). Generally methods of estimating the command device's initial location or repeatedly estimating the command device location as depicted in FIGS. 7A-F involve passive registration components and markers that can be quickly and easily deployed to an operating area such as an operating room, a tent in a field hospital, or an operating area in a large open medical triage scenario. Such techniques are desirable in some scenarios where the cost, administrative difficulty, or delay is too great to use more active location schemes such as RF indoor positioning using beacons.

Figure 8:
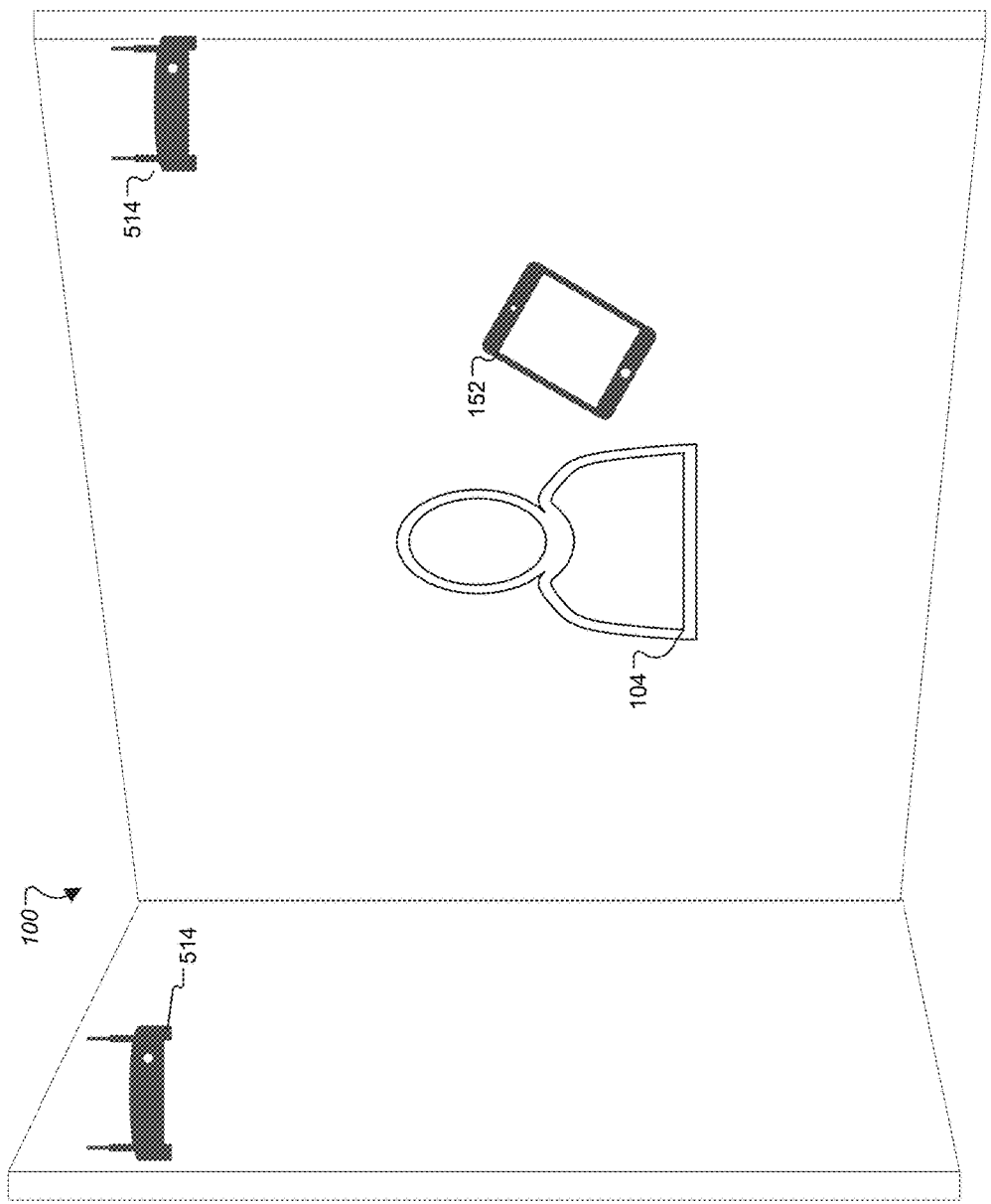
FIG. 8 depicts a similar cutaway view of an operating area having location beacons.

FIG. 8 depicts cutaway view of an operating area having location beacons 514, which as shown are placed generally above the height of a user 104 who will operate command device 152. Such beacons represent an alternative version to determining the command device 152 location, both when estimating the initial location and when repeatedly estimating the current location of command device 152 as discussed above. Visual light or RF beacons may be employed, or other types of beacons such as sound or magnetic. Generally RF beacons may be received by devices outside of their operating area, but an appropriate indoor positioning protocol, such as Bluetooth Indoor Positioning, is employed in these embodiments to ensure that the command device location is determined relative to the beacon using either multiple beacons signal strengths or transmission time delays.

Referring generally, to the forgoing description, as used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the present invention in order that the detailed description of the invention that follows may be better understood. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

Although the present invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A method of pairing a command device to a remotely controlled medical system, the method comprising:
    (a) providing a registration component at a designated location in an operating area, the registration component having a unique identifier associated with the operating area;
    (b) causing the command device to obtain the unique identifier from the registration component in a manner only allowed when the command device is within a designated proximity to the registration component;
    (c) sending a request from the command device to register for control of medical equipment associated with the registration component, and receiving a registration confirmation;
    (d) while registered for control of medical equipment, transmitting commands from the command device for controlling the medical equipment;
    (e) repeatedly estimating the location of the command device based on input from one or more sensors on the command device; and
    (f) repeatedly checking the estimated location and in response to the estimated location being outside a designated area associated with the operating area, deregistering the command device from control of the medical equipment.

2. The method of claim 1 further comprising determining an initial location for the command device, and further in which repeatedly estimating the location of the command device comprises estimating the location based on tracking movement relative to the determined initial location.

3. The method of claim 2 in which determining the initial location for the command device comprises determining the initial location relative to one or more registration markers by recognizing at least one of the registration markers using a camera on the command device.

4. The method of claim 3, in which determining the initial location further comprises estimating a distance from a respective registration marker based on a registration marker measurement as viewed by the camera.

5. The method of claim 2 in which determining the initial location for the command device comprises determining the initial location relative to one or more beacon LED arrangements positioned in the operating area using one or more cameras on the command device.

6. The method of claim 2 in which repeatedly estimating the location of the command device further comprises determining the estimated locations relative to one or more registration markers by recognizing at least one of the registration markers using a camera on the command device.

7. The method of claim 2 further comprising checking whether the estimated location is within a designated proximity of a respective medical device in the operating area, and if so updating a device control interface presented on the command device to present controls for the respective medical device.

8. The method of claim 1 in which repeatedly estimating the location of the command device further comprises estimating the location based on at least an onboard accelerometer of the command device.

9. The method of claim 1 in which repeatedly estimating the location of the command device further comprises using data from multiple RF beacons in the operating area.

10. The method of claim 1 in which repeatedly estimating the location of the command device further comprises using signal strength data from one or more radio-frequency receivers of the command device, the signal strength data associated with one or more of designated transmitters in or near the operating area.

11. A system for pairing a command device to a remotely controlled medical system, the system comprising:
    a controller having a communications interface operable to control one or more external medical devices;
    a registration component configured to store a unique identifier associated with an operating area, the registration component configured to display or broadcast the unique identifier;
    a command device operable to be in communication with the controller, the command device including a user interface device, a processor operably coupled to the user interface device, and one or more sensors operably coupled to the processor, the processor programmed to cause at least one of the one or more sensors to read or receive the unique identifier when placed within a designated proximity or physical relationship to the registration component, and programmed to receive commands entered at the user interface device and communicate the commands to the controller with the unique identifier; and
    the command device operable to detect with at least one of the one or more sensors when the command device is removed from a designated area surrounding the controller, and in response, cease sending commands from the command device to the one or more external medical devices.

12. The system of claim 11 in which the command device is further operable to repeatedly estimate the location of the command device based on input from the one or more sensors on the command device; and wherein the command device or controller is operable to repeatedly check the estimated location and in response to the estimated location being outside a designated area associated with the operating area, deregister the command device from control of the one or more external medical devices.

13. The system of claim 12 in which the command device is further operable to determine an initial location for the command device relative to the registration component, and further in which repeatedly estimating the location of the command device comprises estimating the location based on tracking movement relative to the determined initial location.

14. The system of claim 13 in which determining the initial location for the command device comprises determining the initial location relative to one or more registration markers by recognizing at least one of the registration markers using a camera on the command device.

15. The system of claim 14, in which determining the initial location further comprises estimating a distance from a respective registration marker based on a registration marker dimension as viewed by the camera.

16. The system of claim 12 in which repeatedly estimating the location of the command device further comprises estimating the position based on at least an onboard accelerometer of the command device.

17. The system of claim 12 in which repeatedly estimating the location of the command device further comprises determining the estimated locations relative to one or more registration markers by recognizing at least one of the registration markers using a camera on the command device.

18. The system of claim 12 in which the command device is further programmed to check whether the estimated location is within a designated proximity of a respective medical device in the operating area, and if so, update a device control interface presented on the command device to present controls for the respective medical device.

19. The system of claim 12 in which the command device is programmed to repeatedly estimate the location of the command device using data from multiple RF beacons in the operating area.

20. The system of claim 11 in which the registration component includes one or more beacon LED arrangements.

* * * * *